US00RE43702E

(19) United States
(12) Reissued Patent
Wolleschensky

(10) Patent Number: US RE43,702 E
(45) Date of Reissued Patent: Oct. 2, 2012

(54) MICROSCOPE WITH HEIGHTENED RESOLUTION AND LINEAR SCANNING

(75) Inventor: Ralf Wolleschensky, Jena (DE)

(73) Assignee: Carl Zeiss MicroImaging GmbH, Jena (DE)

(21) Appl. No.: 12/973,130

(22) Filed: Dec. 20, 2010

Related U.S. Patent Documents

Reissue of:
(64) Patent No.: 7,468,834
Issued: Dec. 23, 2008
Appl. No.: 11/698,279
Filed: Jan. 26, 2007

U.S. Applications:
(63) Continuation of application No. 10/967,348, filed on Oct. 19, 2004, now abandoned, and a continuation of application No. 10/967,343, filed on Oct. 19, 2004, now abandoned.

(30) Foreign Application Priority Data

Jul. 16, 2004 (DE) ..... 10 2004 034 962
Jul. 16, 2004 (DE) ..... 10 2004 034 996

(51) Int. Cl.
*G02B 21/00* (2006.01)
(52) U.S. Cl. ..... 359/370; 359/385; 359/577
(58) Field of Classification Search ..... None
See application file for complete search history.

(56) References Cited

U.S. PATENT DOCUMENTS

| | | | |
|---|---|---|---|
| 5,022,743 | A | 6/1991 | Kino et al. |
| 5,866,911 | A | 2/1999 | Baer |
| 6,028,306 | A | 2/2000 | Hayashi |
| 6,028,360 | A | 2/2000 | Nakamura et al. |
| 6,167,173 | A | 12/2000 | Schoeppe et al. |
| 6,947,127 | B2 | 9/2005 | Wolleschensky et al. |
| 7,009,763 | B1 | 3/2006 | Wolleschensky |
| 2003/0132394 | A1 | 7/2003 | Wolleschensky et al. |
| 2004/0047034 | A1 | 3/2004 | Sander |
| 2004/0051976 | A1 | 3/2004 | Karin et al. |
| 2004/0145752 | A1 | 7/2004 | Angeley |
| 2005/0241653 | A1 | 11/2005 | Van Heugten et al. |

FOREIGN PATENT DOCUMENTS

| | | | |
|---|---|---|---|
| DE | 2360197 | A1 | 6/1975 |
| DE | 19702753 | A1 | 7/1998 |
| DE | 10257237 | A1 | 6/2003 |
| JP | 2005147968 | A | 9/2005 |
| WO | 88 79695 | | 10/1988 |

OTHER PUBLICATIONS

Pawley, James B., "Handbook of Biological Confocal Microscopy," Chapter 29, Section titled "Horizontal Scanning at > 15 Hz," pp. 460-462 (including Figure 1 on p. 460), Plenum Press, New York, Second Edition, 1995.

(Continued)

*Primary Examiner* — Lee Fineman
(74) *Attorney, Agent, or Firm* — Jacobson Holman PLLC

(57) ABSTRACT

Microscope with heightened resolution and linear scanning wherein the sample is illuminated with a first and a second illuminating light, whereby the first illuminating light excites the sample, and the second illuminating light is generated through the refraction of coherent light at a periodic structure and displays a periodic structure in a lateral beam direction and in axial beam direction.

29 Claims, 5 Drawing Sheets

Amended

OTHER PUBLICATIONS

Gustafsson, M., "Doubling the lateral resolution of wide-field fluorescence microscopy using structured illumination," "Three-dimensional and multidimensional microscopy: Image acquisition processing VII," Proceedings of SPIE, vol. 3919 (2000), p. 141-150.
S. W. Hell and J. Wichmann, "Breaking the diffraction resolution limit by stimulated emission: stimulated-emission-depletion fluorescence microscopy," Opt. Lett. 19, 780 (1994).
T. A. Klar, M. Dyba, and S. W. Hell; "Stimulated emission depletion microscopy with an offset depleting beam," Appl. Phys. Let. vol. 78, No. 4, 393 (2001).
Heintzmann, Rainer et al., "Saturated patterned excitation microscopy—A Concept for Optical Resolution Improvement," J. Opt. Soc. Am. A, vol. 19, No. 8, pp. 1599-1609 (2002).
G. Karp (2002): "Cell and Molecular Biology: Concepts and Experiments"; Wiley Text Books (Table of Contents only).
R.P. Haugland (2003): "Handbook of Fluorescent Probes and Research Products," 10th Edition; Molecular Probes Inc. and Molecular Probes Europe BV (preface and Table of Contents only).
Abdul-Karim, M.A. et al., "Automated tracing and change analysis of angiogenic vasculature from in vivo muliphoton confocal image time series," Microvasc. Res., 66:113-125 (2003).
Grossmann, R. et al., "Juxtavascular microglia migrate along brain microvessels following activation during early postnatal development," Glia, 37:229-240 (2002).
Umenishi, F. et al., "cAMP Regulated Membrane Diffusion of a Green Fluorescent Protein-Aquaporin 2 Chimera," Biophys J., 78:1024-1035 (2000).
Gimpl, G. et al., "Cholesterol and steroid hormones: modulators of oxytocin receptor function," Prog. Brain Res., 139:43-55 (2002) (Abstract only).
Zhang et al., "Neurotrophin-Induced Transport of a β-Actin mRNP Complex Increases β-Actin Levels and Stimulates Growth Cone Motility," Neuron, 31:261-275 (2001).
Petersen, M.A. and Dailey, M.E., "Diverse Microglial Motility Behaviors During Clearance of Dead Cells in Hippocampal Slices," Glia, 46:195-206 (2004).
Yamamoto, N. et al., "Real-time imaging of individual fluorescent-protein color-coded metastatic colonies in vivo," Clin. Exp. Metastasis, 20:633-638 (2003).
Bertera, S. et al., "Body window-enabled in vivo multicolor imaging of transplanted mouse islets expressing an insulin-Timer fusion protein," Biotechniques, 35:718-722 (2003).
Brum G et al., "Fast imaging in two dimensions resolves extensive sources of Ca2+ sparks in frog skeletal muscle," J Physiol. 528: 419-433 (2000).
Schmidt H et al., "Mutational analysis of dendritic Ca2+ kinetics in rodent Purkinje cells: role of parvalbumin and calbindin D28k," J Physiol. 551:13-32 (2003).
Egner, "Time multiplexing and parallelization in multifocal multiphoton microscopy," J. Opt. Soc. Am. A, 17: 1192-1201 (2000).
J.W. Goodman, "Introduction to Fourier Optics" (McGraw-Hill 1996), pp. 87-89.
V. Westphal et al., "Laser-diode-stimulated emission depletion microscopy," 82 Applied Physics Letters, No. 18, pp. 3125-3127 (May 5, 2003).
Pawley, Handbook of Biological Confocal Microscopy, Plenum Press, 1944, pp. 461 ff.
J Heintzmann, "Saturated patterned excitation microscopy," J. Opt. Soc. Am. A, vol. 19, No. 8 (2002).

Amended
FIG. 1
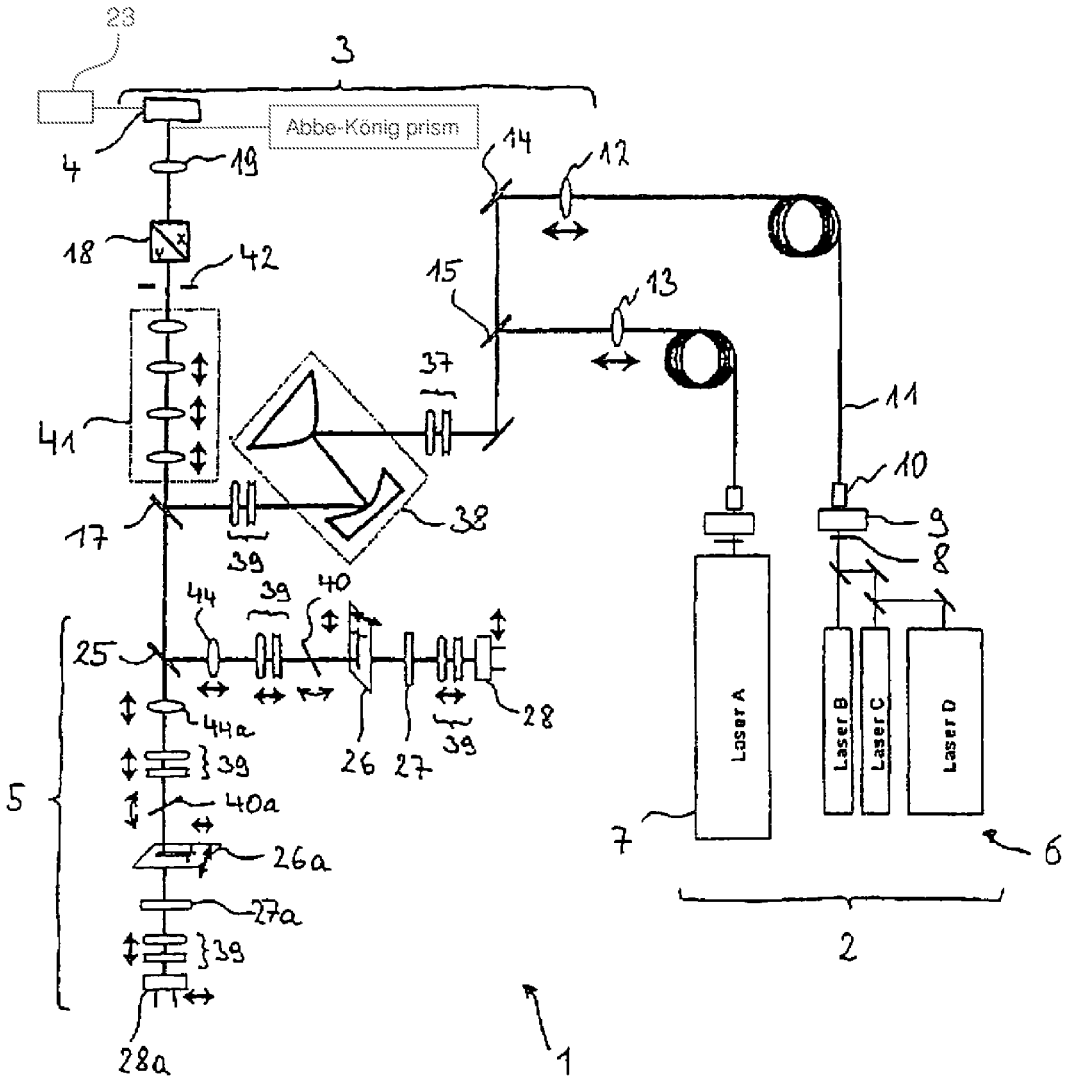

A.)

MICROSCOPE WITH HEIGHTENED RESOLUTION AND LINEAR SCANNING

Matter enclosed in heavy brackets [ ] appears in the original patent but forms no part of this reissue specification; matter printed in italics indicates the additions made by reissue.

CROSS-REFERENCE TO RELATED APPLICATIONS

The present patent application is a continuation of application Ser. No. 10/967,343, filed Oct. 19, 2004 now abandoned and application Ser. No. 10/967,348, filed Oct. 19, 2004, now abandoned both of which are incorporated herein by reference in their entireties.

BACKGROUND OF THE INVENTION

1. Field of the Invention
Not applicable.
2. Related Art
Not applicable.

SUMMARY OF THE INVENTION

Not applicable.

BRIEF DESCRIPTION OF THE DRAWINGS

FIG. 1 is a schematic drawing showing a laser scanning microscope.

DETAILED DESCRIPTION OF THE PREFERRED EMBODIMENTS

Figure 2:
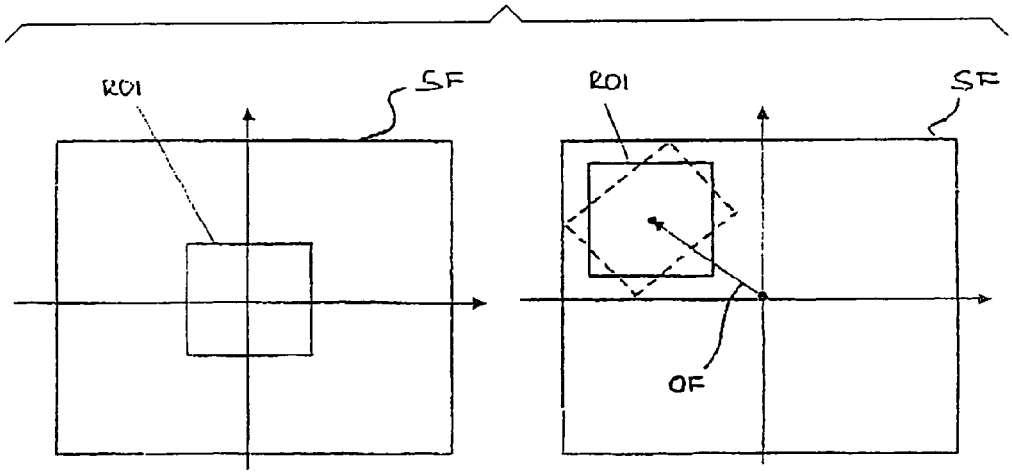
FIG. 2 shows how the zoom optics of the microscope of FIG. 1 can be used to select a region of interest within the maximum available scan field.

The invention will be explained in greater detail below with reference to the drawings.

FIG. 1 schematically shows a laser scanning microscope 1 comprising essentially four components: a radiation source module 2 that generates excitation radiation for laser scanning microscopy; a scanning module 3 that conditions the excitation radiation and suitably deflects it for scanning over a sample; a microscope module 4, for the sake of simplicity shown only schematically, that directs the scanning radiation prepared by the scan module in a microscopic beam path onto a sample; and a detector module 5 that receives and detects optical radiation from the sample. Detector module 5 can, as shown in FIG. 1, be configured so as to be spectrally multi-channeled.

Concerning the general description of a laser scanning microscope that scans point by point, reference is made to DE 19702753 A1 which thus is an integral part of the present description.

Radiation source module 2 generates illumination radiation that is suitable for the laser scanning microscopy, i.e., in particular radiation that can trigger fluorescence.

Depending on the application, the radiation source module has several radiation sources for this purpose. In one depicted embodiment form, two lasers 6 and 7 are provided in radiation source module 2, downstream of which a light valve 8 and an attenuator 9 is arranged and which couple their radiation via a coupling point 10 into a fiber optical waveguide 11. Light valve 8 acts as a deflector with which a reduction of radiation can be effected without it being necessary to switch off the operation of the lasers in laser unit 6 or 7 themselves. Light valve 8 by way of example is configured as an AOTF which in order to switch off radiation deflects the laser beam prior to injection in optical fiber waveguide 11 in the direction of a not-depicted light trap.

In the exemplary depiction of FIG. 1, laser unit 6 has 3 lasers B, C, D, while laser unit 7 contains only one laser A. The depiction thus is exemplary for a combination of single and multiple wave-length lasers which individually or also jointly are coupled to one or more fibers. The coupling can also take place over several fibers simultaneously, the radiation of which subsequently is mixed through a color uniter following passage through an adapting optic. It is thus possible to use extremely varied wave lengths or ranges for the excitation radiation.

The radiation coupled into fiber optic waveguide 11 is drawn together by means of movable collimation optics 12 and 13 through radiation uniting mirrors 14, 15 and is changed with respect to the radiation profile in a beam-forming unit.

Collimators 12, 13 collimate the radiation brought in from radiation source module 2 into scan module 3 into an infinite beam path. This takes place advantageously in each case with the aid of a single lens which as a result of moving along the optical axis under the control of (a not-depicted) central steering unit has a focusing function in that the distance between collimator 12, 13 and the respective end of the fiber optic is modifiable.

From the radially symmetric Gaussian profiled laser beam, as is present after beam uniting mirrors 14, 15, the beam-forming unit, which will be explained in detail later, generates a linear beam that no longer is radially symmetrical but rather is suited in cross section to generate a rectangular illuminating field.

This illuminating beam which is also designated as being line-shaped serves as triggering radiation and is conducted via a main color splitter 17 and a yet to be described zoom optic to a scanner 18. The main color splitter will be discussed later, but it should be mentioned at this point that it has the function of separating the sample radiation returning from microscope module 4 from the triggering radiation.

Scanner 18 deflects the line-shaped beam in one or two axes, after which it is bundled through a scanning objective lens 19 and a tube-shaped lens and an objective lens of microscope module 4 into a focus (not shown) which is situated in a preparation or in a sample. Optical imaging takes place such that the sample is illuminated in a focal line with triggering radiation.

Fluorescence radiation excited in this manner in the line-shaped focus arrives through objective lens and tubular lens of microscope module 4 and scanning objective lens 19 back to scanner 18 so that in the reverse direction there again is a resting beam behind scanner 18. It is therefore also said that the scanner 18 de-scans the fluorescence radiation.

Main color splitter 17 allows the fluorescence radiation in other wave length ranges than the excitation radiation to pass so that it can be redirected via a redirecting mirror (not shown) in the detector module 5 and can then be analyzed. In the embodiment form of FIG. 1, detector module 5 has several spectral channels, i.e., the fluorescence radiation coming from the redirecting mirror is split in a secondary color splitter 25 into two spectral channels.

Each spectral channel has a slit diaphragm 26 which realizes a confocal or partially confocal image with respect to a sample (not shown) and the size of which slit diaphragm establishes the depth of focus with which the fluorescence can be detected. The geometry of slit diaphragm 26 thus determines the cutting plane within the (thick) preparation from which fluorescence radiation is detected.

Slit diaphragm 26 is arranged behind a blocking filter 27 that blocks out undesired excitation radiation which entered into detector module 5. The radiation separated out in this manner which originated from a certain depth section and was fanned out linearly is then analyzed by a suitable detector 28. The second spectral detection channel, which likewise comprises a slit diaphragm 26a, a blocking filter 27a, and a detector 28a, is also constructed analogous to the depicted color channel.

The use of a confocal slit aperture in detector module 5 is only by way of example. A single-point scanner can of course also be realized. Slit diaphragms 26, 26a are then replaced by apertured diaphragms and the beam-forming unit can be omitted. In other respects all optics are configured radially symmetrically for such a construction style. Then of course in place of single-point scanning and detection basically any desired multiple-point arrangements such as point-cloud or Nipkow-disk concepts can be used as will be explained later with the aid of FIGS. 3 and 4. Then, however, it is essential that detector 28 be spatially resolving since parallel capture of several sample points takes place upon the pass of the scanner.

It can be seen in FIG. 1 that the Gaussian beam bundles present behind the movable, i.e., sliding collimators 12 and 13 are united through a ladder of mirrors in the form of beam-uniting mirrors 14, 16 and then in the construction depicted with confocal slit diaphragm are converted into a beam bundle with rectangular beam cross section. In the embodiment form of FIG. 1, a cylinder telescope 37 that is arranged behind an aspherical unit 38 which is followed by cylinder optics 39 is utilized in the beam-forming unit.

After the conversion, there is a beam which in a profile level essentially illuminates a rectangular field with the intensity distribution along the longitudinal field axis not being Gaussian but rather box shaped.

The illumination arrangement with aspherical unit 38 can serve the purpose of uniform filling of a pupil between a tubular lens and an objective lens. In this way the optical resolution of the objective lens can be fully utilized. This variant thus is also advantageous in a single-point or multiple-point scanning microscope system, for example in a line scanning system (in the case of the latter in addition to the axis in which focusing upon or into the sample takes place).

The excitation radiation by way of example conditioned linearly is directed onto main color splitter 17. In a preferred embodiment form, the latter is configured as a spectrally neutral splitter mirror in accordance with DE 10257537 A1, the full disclosure content of which is incorporated here. The term "color splitter" thus also comprises non-spectrally acting splitter systems. In place of the described spectrally-independent color splitter, a homogenous neutral splitter (for example 50/50, 70/30, 80/20, or the like) or a dichroitic splitter can also be used. In order for a selection to be possible depending on the application, the main color splitter preferably is provided by a mechanism which facilitates an easy change, for example through a corresponding splitter wheel that contains individual interchangeable splitters.

The dichroitic main color splitter is particularly advantageous if coherent, i.e., directional radiation is to be detected such as, for example, reflection, Stokesian or anti-Stokesian Raman spectroscopy, coherent Raman processes of relatively high order, general parametric non-linear optical processes such as second harmonic generation, third harmonic generation, sum frequency generation, and double and multiple photon absorption or fluorescence. Several of these methods of non-linear optical spectroscopy require the use of two or more laser beams which are superimposed collinearly. In so doing, the depicted beam unification of the radiation of several lasers proves to be particularly advantageous. Fundamentally the dichroitic beam divider which is widely used in fluorescence microscopy can be used. For Raman microscopy, it is also advantageous for holographic notch splitters or filters to be used in front of the detectors in order to suppress the Rayleigh scattering portion.

In the embodiment form of FIG. 1, the excitation radiation or illumination radiation is brought to scanner 18 through motor-controlled zoom optics 41. Thus the zoom factor can be adapted and the scanned field of view is infinitely variable in a certain adjustment range. Particularly advantageous are zoom optics in which the pupil position remains in a continuous tuning process during adjustment of the focus location and of the imaging scale. The three motorized degrees of freedom depicted in FIG. 1, symbolized by arrows, of zoom optics 41, correspond precisely to the number of degrees of freedom which are provided for adaptation of the three parameters imaging scale, focus location, and pupil location. Particularly preferred are zoom optics 41, at the exit-side pupil of which a fixed diaphragm 42 is arranged. In a practical simple realization, diaphragm 42 can also be predetermined through the limitation of the mirror surface of scanner 18. Output-side diaphragm 42 with zoom optics 41 causes a predefined pupil diameter to always be imaged on scanning objective lens 19 independent of the setting of the zoom enlargement. Thus the objective lens pupil continues to be fully illuminated regardless of the setting of zoom optics 41. The use of a self-contained diaphragm 42 advantageously prevents the occurrence of undesired scatter radiation in the area of scanner 18.

Working together with zoom optics 41 is cylinder telescope 37 which is likewise motorized and is arranged in front of aspherical unit 38. In the embodiment form of FIG. 2 this is selected as a result of a compact construction but does not have to be such.

If a zoom factor smaller than 1.0 is desired, cylinder telescope 37 is automatically swung into the optical beam path. If zoom objective lens 41 is made smaller, incomplete illumination of aperture diaphragm 42 is prevented. Swivelable cylinder telescope 37 thus ensures that even at zoom factors smaller than 1, i.e., independent of the setting of zoom optics 41 an illumination line of constant length is always present at the site of the objective lens pupil. In comparison to a simple visual field zoom, laser performance losses in the illumination beam are thus avoided.

Since upon swiveling the cylinder telescope 37, a jump in image brightness in the illumination line is unavoidable, it is provided in the (not depicted) control unit that the advance speed of scanner 18 or an amplification factor of the detectors in detector module 5 must be correspondingly adjusted in the case of activated cylinder telescope 37 in order to hold the image brightness constant.

Alongside motor-driven zoom optics 41 and motor-activated cylinder telescope 37, remote controllable adjustment elements are also provided in detector module 5 of the laser scanning microscope of FIG. 1. For compensation of longitudinal chromatic aberrations, round optics 44 as well as cylinder optics 39 by way of example are provided in front of the slit diaphragm and cylinder optics 39 are provided directly in front of detector 28, each of which can be shifted in axial direction by motor.

In addition to compensation, a correction unit 40 is provided which will be described briefly below.

Slit diaphragm 26 together with round optics 44 arranged in front and first cylinder optics 39 likewise arranged in front and second cylinder optics arranged behind form a pinhole objective lens of detector arrangement 5, with the pinhole being realized here through slit diaphragm 26. In order to avoid an undesired detection of excitation radiation reflected in the system, blocking filter 27 is arranged in front of second cylinder lens 39, blocking filter 27 having suitable spectral properties in order to allow only the desired fluorescence radiation to reach detector 28, 28a.

A change of color splitter 25 of blocking filter 27 unavoidably is accompanied by a certain tilt error or wedge error upon swiveling into place. The color splitter can cause an error between the sample range and slit diaphragm 26, and blocking filter 27 can cause an error between slit diaphragm 26 and detector 28. In order to prevent a readjustment of the position of slit diaphragm 26 or detector 28 from being necessary, a plane-parallel plate 40 is arranged between round optics 44 and slit diaphragm 26, i.e., in the imaging beam path between the sample and detector 28 which under the control of a controller can be brought into various inclination positions. Plane-parallel plate 40 in addition is adjustably mounted in a suitable holding device. The second spectral detection channel likewise comprises a plane-parallel plate 40a arranged between round Optics 44a and slit diaphragm 26a, i.e., in the imaging beam path between the sample and detector 28a.

FIG. 2 shows how with the aid of zoom optics 41, a region of interest ROI can be selected within the maximum scan field SF which is available. If one allows the steering of scanner 18 to be such that the amplitude does not change, as is required by way of example for resonance scanners, an enlargement greater than 1.0 set at the zoom optics will cause a narrowing of the selected region of interest ROI centered around the optical axis of scan field SF.

Resonance scanners are described by way of example in Pawley, Handbook of Biological Confocal Microscopy, Plenum Press, 1944, pages 461 ff. If the scanner is steered such that it scans a field asymmetrically to the optical axis, i.e., to the neutral position of the scanner mirror, an offset shift OF of the selected region ROI will be obtained in connection with a zoom effect. As a result of the already mention effect of scanner 18 to de-scan and as a result of passing through zoom optics 41 a second time, the selection of region of interest ROI in the detection beam path is again picked up in the direction toward the detector. Thus any desired selection within scan field SF can be selected as region ROI. In addition, images can be made for various selections of range ROI, and they can then be merged into a high resolution image.

If one wishes not only to shift the selected region ROI with respect to the optical axis by an offset OF but rather also to rotate it, an embodiment form is advantageous which provides in a pupil of the beam path between main color splitter 17 and sample 23 an Abbe-König prism that as is known results in a rotation of the image field. The latter is also picked up again in the direction of the detector. Now images with various offset shifts OF and various angles of rotation can be measured and then computed into a high-resolution image, by way of example in accordance with an algorithm as is described in the publication Gustafsson, M., "Doubling the lateral resolution of wide-field fluorescence microscopy using structured illumination," in "Three-dimensional and multidimensional microscopy: Image acquisition processing VII," Proceedings of SPIE, Vol. 3919 (2000), p. 141-150.

Figure 3:
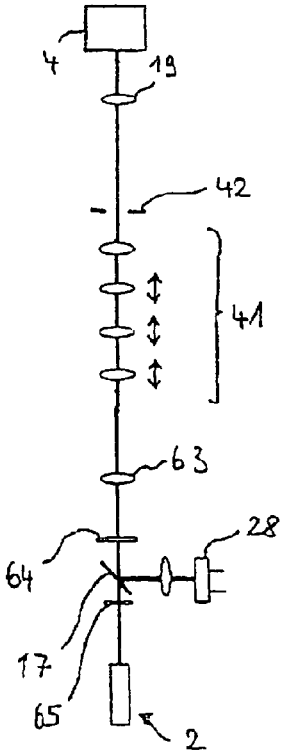
FIG. 3 is a schematic drawing showing a second possible construction for a laser scanning microscope in which a Nipkow disk approach is realized.

FIG. 3 shows a further possible construction for a laser scanning microscope 1 in which a Nipkow disk approach is realized. Light-source module 2, which is depicted in FIG. 3 in greatly simplified form, illuminates a Nipkow disk 64, as it is described by way of example in U.S. Pat. No. 6,028,306, WO 88 079695, or DE 2360197 A1, via a minilens array 65 through main color splitter 17. The pinholes of the Nipkow disk which are illuminated via minilens array 65 are imaged in the sample situated in microscope module 4. In order to make it possible to vary the image size on the sample side here as well, zoom optics 41 are again provided.

In the Nipkow scanner, in contrast to the construction of FIG. 1, illumination takes place in the passage through main color splitter 17 and the beam to be detected is reflected out. In addition, in contrast to FIG. 2 detector 28 is now configured for spatial resolution so that the multiple-point illumination achieved with Nipkow disk 64 is also scanned correspondingly parallel. Furthermore, suitably fixed optics 63 with positive refracting power are arranged between Nipkow disk 64 and zoom optics 41 which convert the beam exiting in divergent manner through the pinholes of Nipkow disk 64 into suitable bundle diameter. Main color splitter 17 for the Nipkow configuration of FIG. 3 is a classic dichroitic beam splitter, i.e., not the beam splitter mentioned above with slit-shaped or point-shaped reflecting region.

Zoom optics 41 correspond to the construction explained above, with scanner 18, of course, being made superfluous by Nipkow disk 64. It can nevertheless be provided if one wishes to make the selection explained with the aid of FIG. 2 of a region ROI. The same applies to the Abbe-König prism.

Figure 4:
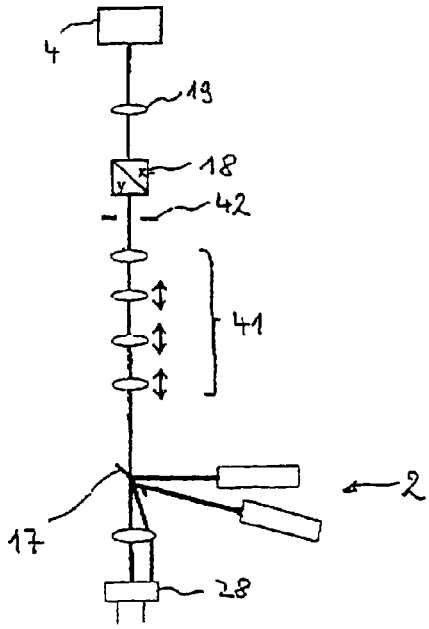
FIG. 4 is a schematic drawing showing a third possible construction for a laser scanning microscope with multiple-point scanning.

An alternative approach with multiple-point scanning is shown schematically in FIG. 4 in which several light sources beam obliquely into the scanner pupil. Here also through the use of zoom optics 41 for imaging between main color splitter 17 and scanner 18, a zoom function can be realized as depicted in FIG. 2. Through simultaneous beaming of light bundles at various angles in a plane conjugated to the pupil, light spots are generated in a plane conjugated to the objective lens plane which simultaneously are brought by scanner 18 over a subregion of the entire object field. The image formation takes place through evaluation of all subimages on a spatially resolving matrix detector 28.

Another possible embodiment form is multiple point scanning as described in U.S. Pat. No. 6,028,306, the disclosures of which are incorporated here in full. Here also a spatially resolving detector 28 is provided. The sample is then illuminated through a multiple-point light source which is realized through a beam expander with downstream microlens array which illuminates a multiple aperture plate such that a multiple-point light source is thereby realized.

Figure 5:
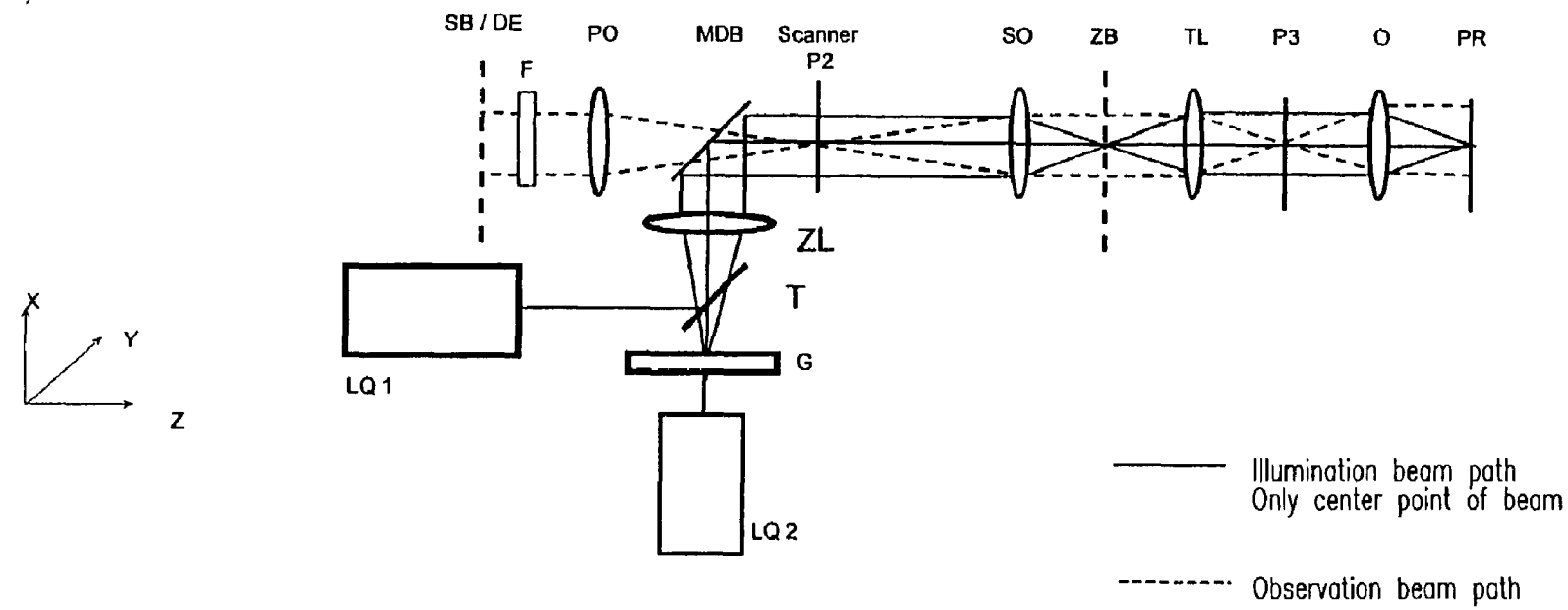
FIG. 5 is a schematic drawing showing a light source arranged behind a grid.

FIG. 5 shows a light source LQ2 which is arranged behind a grid G. [Light source LQ2] Light source LQ2 can be united via a splitter T with a light source LQ1 for excitation of fluorescence. Both light sources are imaged through cylinder optics ZL as a line on the sample. LQ1 generates a homogenous line on/in the sample PR. As a result of the effect of grid G, LQ2 generates a periodically modulated line.

A main color splitter MDB separates the illumination from the detection. The MDB can be configured as a dichroitic color splitter or as a strip mirror corresponding to DE102575237. In the latter case, the MDB must be arranged in the vicinity of a pupil plane of the microscope arrangement. For the mirroring in of LQ1 and of the zero$^{th}$ order of LQ2, it has a centrally arranged strip mirror (along the y-axis), and for LQ2 it has two strip mirrors arranged decentrally along the y axis corresponding to the grid frequency.

A scanner P2 serves to move the illumination line over sample PR. Also arranged are scanning optics SO, tubular lens TL for transfer of an intermediate image ZB onto the objective pupil P3, objective lens O in same beam path as well as pinhole optics PO, filter F, and detector DE or slit diaphragm SB in the detector beam path.

LQ1 and LQ2 are connected to a control unit for synchronization of the sample illumination with LQ1 and LQ2.

Figure 6:
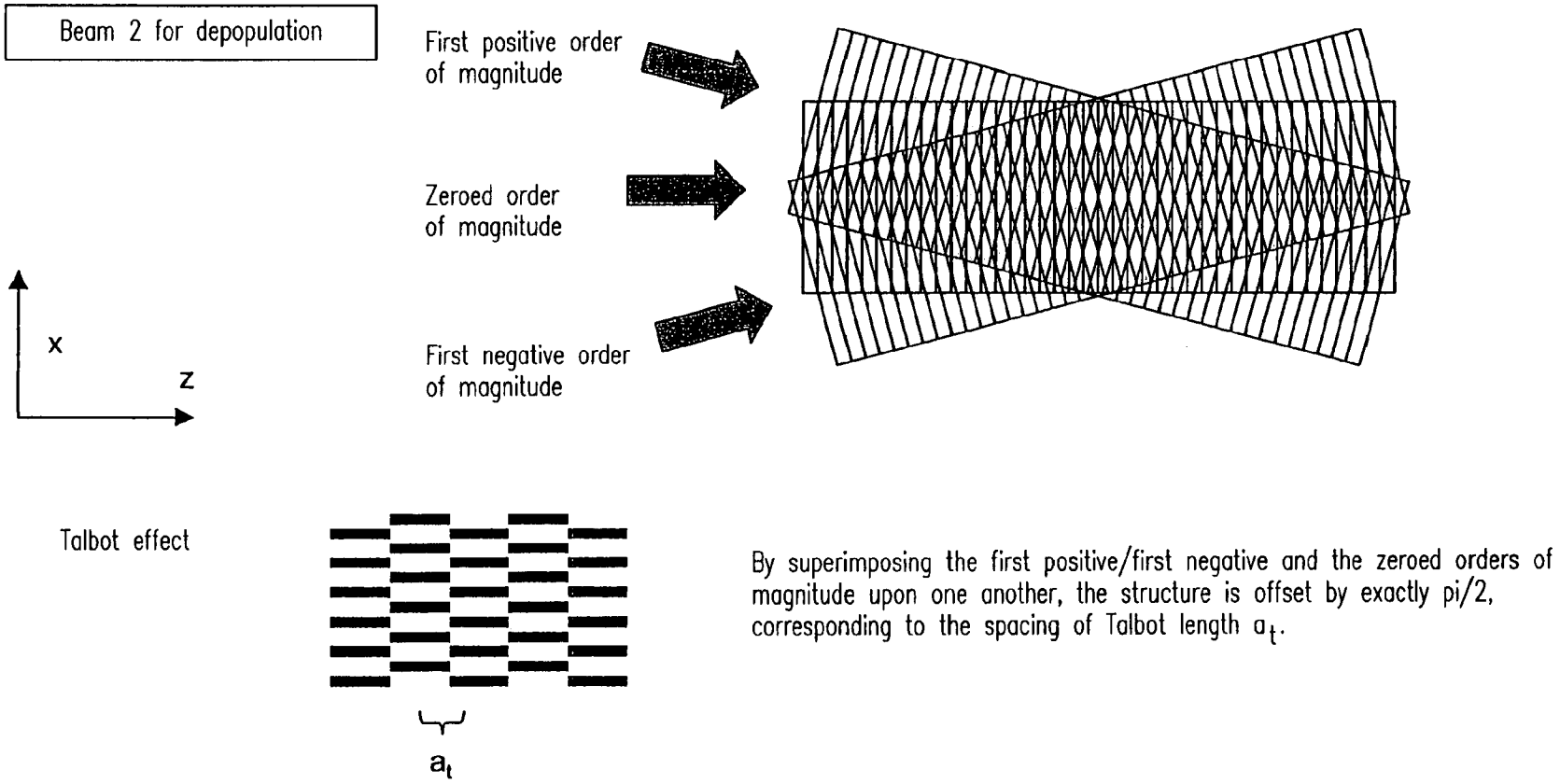
FIG. 6 is a diagram showing how an interference field of the $-1^{st}$, $0^{th}$, or $1^{st}$ order is formed at an amplitude grid G in transmission during irradiation with laser light.

FIG. 6 depicts how an interference field of the $-1^{st}$, $0^{th}$, or $1^{st}$ order is formed at an amplitude grid G in transmission during irradiation with laser light. If these interference-capable fields are imaged to a sample, by way of example, in a line-shape, a Talbot structure (literature: Talbot effect) arises in the Z direction. The Talbot effect occurs upon the bending of coherent light at a planar periodic structure of period d. At distances of:

$$z_n = \frac{2nd^2}{\lambda}$$

images of the original structure arise, whereby for odd multiples, the structure is shifted by exactly half of period d of the original structure (Lit.: Lexikon der Optik (Lexicon of Optics), Spektrum Akademie Verlag, 1999, Berlin). Lambda here denotes the wave length and n denotes the whole number multiple of the Talbot plane. In partial image a) of FIG. 6, the so-called Talbot planes (along x) are schematically presented. In the case of the superimposition of the +/−1 and the 0 conjugation order, an offset of the structure results by precisely pi/2 in the distance of Talbot length at.

The depth resolution of the objective lens is computed from:

$$\Delta z = \frac{\pi a^2}{2\lambda},$$

with a being the lateral resolution of the objective lens. Preferably the grid constant of grid G is selected such that a periodic structure in the sample results with $$d = \frac{\sqrt{\pi}\, a}{2}.$$

In this case, the distance between the Talbot planes is equal to the depth resolution of the microscope objective lens.

LQ2 in combination with the grid advantageously serves to suppress fluorescent processes (Lit.: S. W. Hell and J. Wichmann, Opt. Lett. 19, 780; 1994).

Figure 7:
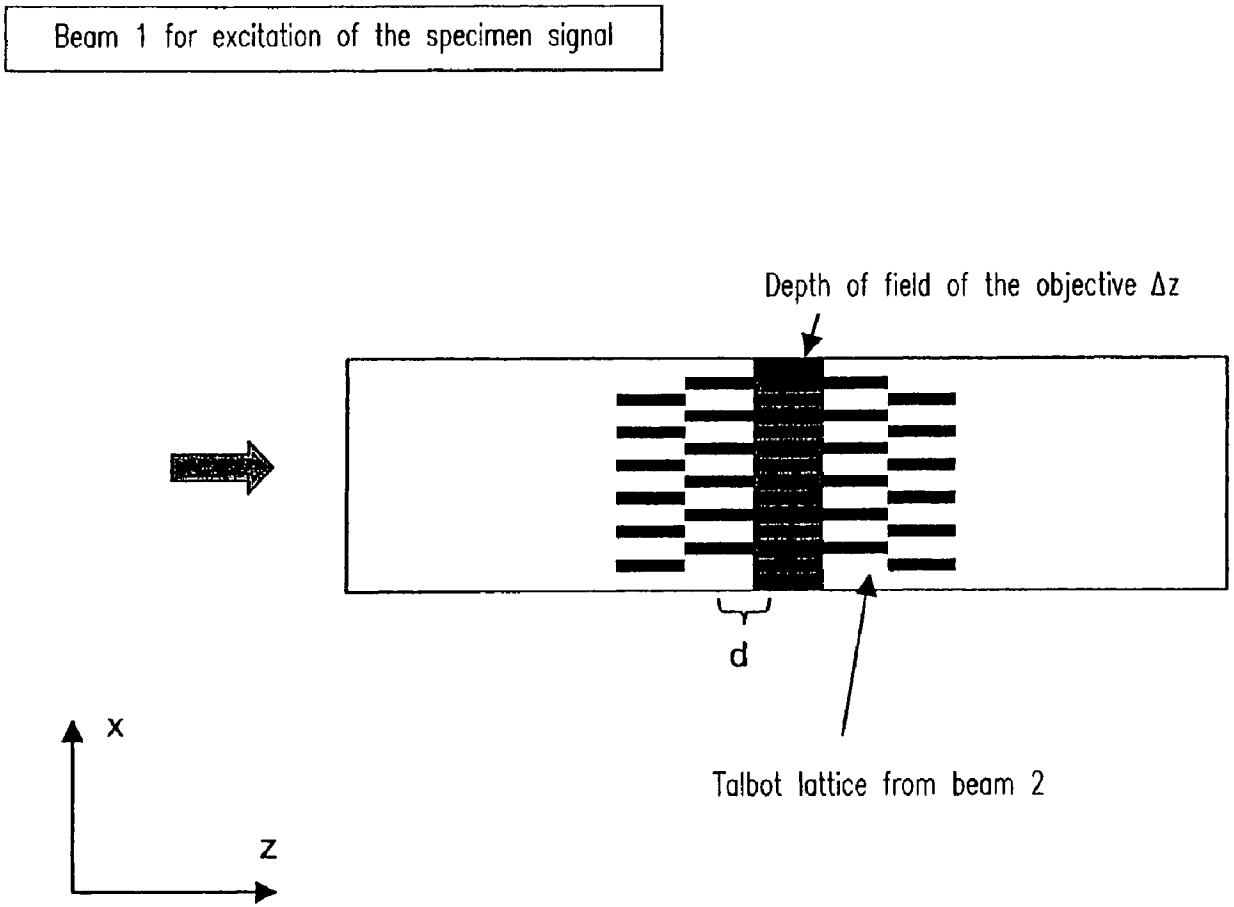
FIG. 7 is a diagram showing a beam line presented in the X-Z direction, which illuminates the sample homogenously in the direction of the arrow along the X axis.

Depopulation mechanisms can by way of example be the stimulated emission (Lit.: T. A. Klar, M. Dyba, and S. W. Hell; Appl. Phys. Let. Vol 78, No.: 4, 393, 2001), the depopulation of the ground state or the purposeful switching of dyes into various emission/absorption conditions. The beam from LQ1 serves to excite fluorescence, In FIG. 7, a beam line of LQ1 is presented in X-Z direction which illuminates the sample homogenously in the direction of the arrow along the X axis. The depth resolution of the objective lens preferably is set identical to the distance between the Talbot planes. The fluorescence activity of the dye molecules is suppressed in the region of the black areas (grid distribution) through illumination patterns in beam (from LQ2) generated by means of a grid.

In the case of stimulated emission, this takes place through the intentional de-energizing of dye molecules through stimulated emission in the region of the black stripes. Thus regions with higher fluorescence intensity (not de-excited) and with lower fluorescence intensity (de-excited) arise. Through detection of the regions of higher intensity, the resolution of an image recording can be heightened. Light sources LQ1 and LQ2 are advantageously pulsed for this purpose. With a pulse from LQ1, the dye is first excited. Before the life of the fluorescence is over (in the nanoseconds range), the de-excitation of the fluorescence molecules by the light distribution of LQ2 takes place. After this, detection of the fluorescence photons takes place through spontaneous emission of the remaining excited fluorescence molecules. Following this, a new excitation can be homogenously effected in a new cycle with a pulse of LQ1.

Upon depopulation of the base state or upon switching of dyes, the suppression of fluorescence activity of dye molecules takes place through the intentional depopulation of the base states or the local alteration of the emission and/or absorption properties of the dye in the region of the black lines. Thus regions arise in which no fluorescence can be excited through the beam of LQ1. Through detection of the fluorescence which is generated in the remaining region which can be excited through LQ1, the resolution of an image recording can be heightened. Light sources LQ1 and LQ2 do not have to be pulsed to accomplish this. With the illumination structure of LQ2, the dye is illuminated upon the depopulation of the base state until no more dye molecules are available in the base state as a result of triplet population (intersystem crossing). In the period of the life of the triplet level (range of milliseconds), the excitation of the fluorescence molecules takes place in the regions previously not irradiated as a result of the light distribution of LQ1. The fluorescence photons are detected as a result of spontaneous emission in the regions previously not irradiated.

Upon the switching of the dye properties with the illumination structure of LQ2, the dye is illuminated until all dye molecules in the region of the illumination structure of LQ2 are switched "dark." Following this in the period of time in which the dye is present with these altered properties, the fluorescence molecules in the regions not previously radiated are excited through the light distribution of LQ1, and the fluorescence photons generated through spontaneous emission are detected.

As a result of the effect of the slit diaphragm as a confocal diaphragm, the depth resolution of the objective lens can in addition be reduced to a region smaller than d (distance between the Talbot levels). Furthermore the SPEM method according to the state of the art can be utilized (Lit.: Saturated patterned excitation microscopy, J. Opt. Soc. Am. A, Vol 19, No. 8, 2002).

It was recognized as advantageous in the arrangement suggested here that as a result of the coherent illumination through a grid, a simultaneous structuring in axial and lateral direction takes place. Thus methods for elevation of resolution can be implemented especially simply, robustly, and efficiently. The simultaneous structuring in lateral and axial direction takes place through the interferometric superimposition of 3 waves (−1, 0, +1) which are planar in at least one axis. The generation of the 3 degrees can take place in various manners, by way of example through radiation of an amplitude grid with a planar wave. Furthermore, special beam splitter arrangements can be utilized (Lit.: High efficiency beam splitter for multifocal multiphoton microscopy, J. of. Microscopy, Vol. 201, Pt3, 2001, page 1), with then only 3 degrees are generated or used.

The described invention represents a significant expansion of the application possibilities of fast confocal laser scanning microscopes. The significance of such a further development can be deduced with the aid of the standard literature of cellular biology and the rapid cellular and subcellular processes described there and the utilized investigation methods with a large number of dyes.

By way of example see:

B. Alberts et al. (2002): Molecular Biology of the Cell; Garland Science.

G. Karp (2002): Cell and Molecular Biology: Concepts and Experiments; Wiley Text Books.

R. Yuste et al. (2000): Imaging Neurons—a Laboratory Manual; Cold Spring Harbor Laboratory Press, New York.

R. P. Haugland (2003): Handbook of Fluorescent Probes and Research Products, 10th Edition; Molecular Probes Inc. and Molecular Probes Europe BV.

The invention is particularly significant for the following processes and events:

Development of Organisms

The described invention is suitable among other things for the investigation of development processes which are distinguished above all by dynamic processes in the range of tenths of a second up to hours. Exemplary applications on the level of associations of cells and of entire organisms are described here by way of example:

Abdul-Karim, M. A. et al. describe in 2003 in Microvasc. Res., 66:113-125 a long-term analysis of blood vessel changes in a living animal with fluorescence images being taken at intervals over several days. The 3D records were evaluated with adaptive algorithms in order to represent the movement trajectories schematically.

Soll, D. R. et al. describe in 2003 in Scientific World Journ. 3:827-841 a software-based analysis of movement of microscopic data of nuclei and pseudopods of living cells in all three spatial dimensions.

Grossmann, R. et al. describe in 2002 in Glia, 37:229-240 a 3D analysis of the movements of microglia cells of rats with the data being captured over a period of up to 10 hours. Simultaneously rapid reactions of the glia also occur following traumatic damage so that a high data rate and corresponding data volumes occur.

This relates in particular to the following areas of emphasis:

Analysis of living cells in a 3D environment whose neighboring cells react sensitively to laser illumination and which must be protected from the illumination of the 3D ROI;

Analysis of living cells in a 3D environment with markings which are to be intentionally bleached through laser illumination, for example FRET experiments;

Analysis of living cells in a 3D environment with markings which are to be intentionally bleached through laser illumination and simultaneously also observations are to be made outside of the ROI, for example FRAP and FLIP experiments in 3D;

Targeted analysis of living cells in a 3D environment with markings and pharmaceuticals which demonstrate manipulation-caused changes as a result of laser illumination, for example activation of transmitters in 3D;

Targeted analysis of living cells in a 3D environment with markings which demonstrate manipulation-caused color changes as a result of laser illumination, for example paGFP, Kaede;

Targeted analysis of living cells in a 3D environment with very weak markings which require for example an optimal balance of confocality and detection sensitivity;

Living cells in a 3D tissue association with varying multiple markings, for example CFP, GFP, YFP, DsRed, HcRed, and the like;

Living cells in a 3D tissue association with markings which demonstrate function-dependent color changes, for example Ca+ markers Living cells in a 3D tissue association with markings which demonstrate development-caused color changes, for example transgenic animals with GFP Living cells in a 3D tissue association with markings which demonstrate manipulation-caused color changes as a result of laser illumination, for example paGFP, Kaede;

Living cells in a 3D tissue association with very weak markings which require a restriction of confocality in favor of detection sensitivity;

The last mentioned point in combination with the preceding ones.

Transport Events in Cells

The described invention is excellently suited for investigation of intercellular transport events since in such investigations quite small motile structures, for example proteins, with high speed (for the most part in the range of hundredths of a second) must be represented. In order to capture the dynamics of complex transport events, applications such as FRAP and ROI bleaching are also often utilized. Examples of such studies are described here by way of example:

Umenishi, F. et al. describes in 2000 in Biophys J., 78:1024-1035 an analysis of the spatial motility of aquaporin in GFP transfected culture cells. For this purpose, points in the cell membranes were intentionally locally bleached and the diffusion of the fluorescence in the vicinity was analyzed.

Gimpl, G. et al. describe in 2002 in Prog. Brain Res., 139:43-55 experiments with ROI bleaching and fluorescence imaging for the analysis of mobility and distribution of GFP marked oxytocin receptors in fibroblasts, with very high requirements with respect to spatial positioning and resolution and the direct temporal succession of bleaching and imaging.

Zhang et al. describe in 2001 in Neuron, 31:261-275 live cell Imaging of GFP transfected nerve cells, with the movement of granuli being analyzed through combined bleaching and fluorescence imaging. The dynamics of the nerve cells in this process place high requirements for the speed of the imaging.

Interactions of Molecules

The described invention is particularly suited for the representation of molecular and other subcellular interactions. In this process, very small structures with high speed (in the range of hundredths of a second) must be represented. In order to resolve the spatial position required for the interaction, indirect techniques such as FRET with ROI bleaching also must be used. Exemplary applications are described here:

Petersen, M. A. and Dailey, M. E. describe in 2004 in Glia, 46:195-206 a two-channel imaging of living hippocampus cultures of rats with the two channels being designed for the markers lectin and sytox in 3D and over a relatively long period of time.

Yamamoto, N. et al. describe in 2003 in Clin. Exp. Metastasis, 20:633-638 two-color imaging of human fibrosarcoma cells in which green and red fluorescent protein (GFP and RFP) were observed simultaneously in real time.

Bertera, S. et al. describe in 2003 in Biotechniques, 35:718-722 a multicolor imaging of transgenic mice marked with timer reporter protein which changes its color following synthesis from green to red. The image is taken as a rapid series 3-dimensionally in the tissue of the living animal.

Signal Transmission Between Cells

The described invention is outstandingly suited for the investigation of for the most part extremely fast signal transmission events. These for the most part neurophysiologic events place the highest of requirements for temporal resolution since the activities mediated through ions take place in the range of hundredths of a second to smaller than a thousandth of a second. Exemplary applications of investigations in the muscular or nerve system are described below:

Brum G et al. describe in 2000 in J Physiol. 528: 419-433 the localization of rapid Ca+ activities in muscle cells of the frog after irritation with caffeine as transmitter. The localization at micrometer-precise resolution was possible only through the use of a fast confocal microscope.

Schmidt H et al. describe in 2003 in J Physiol. 551:13-32 an analysis of Ca+ ions in nerve cell projections of transgenic mice. The investigation of fast Ca+ transients in mice with altered Ca+ binding proteins could be carried out only with high-resolution confocal microscopy since even the localization of the Ca+ activity within the nerve cell and its precise temporal kinetics plays an important role.

I claim:

1. Scanning optical microscope with heightened resolution, comprising:

first means for generating a first illumination light for illuminating and exciting fluorescence in a sample, second means for generating a second illumination light for illuminating the sample, the second illumination light having a spatially periodic structure in the sample in a lateral beam direction and in an axial beam direction, wherein the second means generates the second illumination light by interference of at least three coherent, partial beams in the sample.

2. Microscope according to claim 1, wherein the microscope is a light grid microscope with linear scanning.

3. Microscope according to claim 1, further comprising means for spatially superimposing patterns created by the first and second illumination lights in the sample, wherein a return of an excited state takes place in the sample in the regions of the second illumination light pattern.

4. Microscope according to claim 1, wherein the first and the second illumination lights are laser beams.

5. Microscope according to claim 1, further comprising means for moving the first and second illumination lights jointly over the sample.

6. Microscope according to claim 1, wherein the first and second illumination lights are linear.

7. Microscope according to claim 1, wherein the second means includes a periodic structure that generates the second illumination light through coherent superimposition of several orders of refraction.

8. Microscope according to claim 7, wherein the second means further includes a grid for generating the orders of refraction.

9. Microscope according to claim 8, wherein the grid generates a Talbot grid effect.

10. Microscope according to claim 9, further comprising a microscope objective lens having a depth resolution in the range of the distance between the Talbot planes.

11. Microscope according to claim 1, wherein at least one of the first means and the second means includes at least one pulsed laser for generating at least one of the first and second illumination lights.

12. Method of operating a microscope according to claim 1, comprising generating a depopulation and an excitation in an alternating manner in the sample.

13. Method according to claim 12, wherein the excitation takes place following the depopulation.

14. Method according to claim 12, wherein the depopulation takes place following the excitation.

15. Method according to claim 12, wherein the first and second means of the microscope includes two pulsed lasers for the generation of the first and the second illumination lights, and wherein the method includes the step of operating the two pulsed lasers in a synchronized matter to cause the excitation and the depopulation to take place alternatingly in the sample.

16. Method according to claim 12, further comprising the step of adjusting the optical resolution of the microscope.

17. Method according to claim 12, wherein the second means includes a periodic structure that generates the second illumination light through refraction of coherent light, the method further including the step of varying the frequency of the periodic structure to adjust the optical resolution.

18. Method according to claim 12, wherein the microscope includes a microscope objective lens and the second means includes a periodic structure that generates the second illumination light through refraction of coherent light, and wherein the method further includes the step of switching of the periodic structure upon switching of the microscope objective lens.

19. Method according to claim 12, wherein the second means includes a periodic structure that generates the second illumination light through refraction of coherent light, and the periodic structure is a grid, and wherein the method further comprises the step of switching the grid in the second illumination light.

20. Method for studying developmental processes, comprising the step of: studying dynamic processes in a range of tenths of a second up to hours, on a level of cell associations and entire organisms, using a light grid microscope according to claim 1.

21. Method for studying intercellular transport events, comprising the step of: representing small motile structures with high speed, using a light grid microscope according to claim 1.

22. Method for representing rapid signal transmission events, comprising the step of: representing neurophysiologic events with high temporal resolution in studies in a muscle and nerve system, using a light grid microscope according to claim 1.

23. Scanning optical microscope with heightened resolution, comprising:

first means for generating a line-shaped first illumination light for illuminating and exciting fluorescence in a sample, second means for generating a line-shaped second illumination light for illuminating the sample, the second illumination light having a spatially periodic structure in the sample in a lateral beam direction and in an axial beam direction, wherein the lateral beam direction is oriented longitudinally with respect to the line-shape of the second illumination light, and wherein the second means generates the second illumination light by interference of at least three coherent, partial beams in the sample.

*24. Scanning optical microscope with heightened resolution, comprising:*

*means for generating a line-shaped illumination light for illuminating a sample by interference of at least three coherent, partial beams in the sample, the illumination light having a spatially periodic structure in the sample in a lateral beam direction and in an axial beam direction, wherein the lateral beam direction is oriented longitudinally with respect to the line-shape of the illumination light;*

*optics for imaging the illumination light onto the sample to select a region of interest; and*

*a rotation device for rotating the illumination light relative to the sample to rotate the region of interest.*

*25. Microscope according to claim 24, wherein the means for generating an illumination light includes a laser light source and a periodic structure illuminated by the laser light source, wherein the periodic structure generates the illumination light through coherent superimposition of several orders of refraction.*

*26. Microscope according to claim 25, wherein the periodic structure comprises a grid for generating the orders of refraction.*

*27. Microscope according to claim 24, wherein the rotation device is an Abbe-König prism.*

*28. Microscope according to claim 24, further comprising means for scanning the illumination light over the sample.*

*29. Microscope according to claim 24, wherein the spatially periodic structure of the illumination light suppresses at least a portion of excitation fluorescence emitted by the sample.*

* * * * *